US011715553B2

(12) United States Patent
Chittajallu et al.

(10) Patent No.: US 11,715,553 B2
(45) Date of Patent: Aug. 1, 2023

(54) METHODS, DEVICES AND SYSTEMS FOR ESTIMATING NUTRITIONAL ELEMENT CONTENT IN FOODS

(71) Applicant: ROCHE DIABETES CARE, INC., Indianapolis, IN (US)

(72) Inventors: Siva Chittajallu, Indianapolis, IN (US); Rene Valverde-Ventura, Carmel, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 401 days.

(21) Appl. No.: 16/642,306

(22) PCT Filed: Aug. 30, 2018

(86) PCT No.: PCT/US2018/048748
§ 371 (c)(1),
(2) Date: Feb. 26, 2020

(87) PCT Pub. No.: WO2019/046530
PCT Pub. Date: Mar. 7, 2019

(65) Prior Publication Data
US 2021/0074404 A1 Mar. 11, 2021

Related U.S. Application Data
(60) Provisional application No. 62/552,587, filed on Aug. 31, 2017.

(51) Int. Cl.
*G16H 20/60* (2018.01)
*G16H 20/17* (2018.01)
(Continued)

(52) U.S. Cl.
CPC .......... *G16H 20/60* (2018.01); *A61B 5/14532* (2013.01); *A61B 5/7475* (2013.01); *G16H 20/17* (2018.01)

(58) Field of Classification Search
None
See application file for complete search history.

(56) References Cited

U.S. PATENT DOCUMENTS 5,454,721 A * 10/1995 Kuch ................. G09B 19/0092
434/428
2010/0198142 A1 8/2010 Sloan et al.
2016/0163037 A1* 6/2016 Dehais ................. G06K 9/6267
382/110

FOREIGN PATENT DOCUMENTS

WO WO-2007023619 A1 * 3/2007 ......... G09B 19/0092
WO 2010091129 A1 8/2010
(Continued)

OTHER PUBLICATIONS

Duke, David L. "Intelligent Diabetes Assistant: A Telemedicine System for Modeling and Managing Blood Glucose." Order No. 3470171 Carnegie Mellon University, 2010. Ann Arbor: ProQuest. Web. Mar. 6, 2023. (Year: 2010).*
(Continued)

*Primary Examiner* — Lena Najarian

(57) ABSTRACT

Systems and methods are provided for improving nutritional element content estimates from one or more individuals and/or determining a therapy or treatment based on a nutritional element content estimate and improving diabetes management. The systems and methods include a therapy or treatment display based on at least one nutritional element content estimate and at least one proficiency index respectively assigned to an individual to improve accuracy and reliability when estimating nutritional element content in foods and/or therapy or treatment based therefrom.

3 Claims, 4 Drawing Sheets

(51) Int. Cl.
 *A61B 5/145* (2006.01)
 *A61B 5/00* (2006.01)

(56) References Cited

FOREIGN PATENT DOCUMENTS

| WO | 2013123416 A2 | 8/2013 |
| WO | 2015000890 A1 | 1/2015 |
| WO | 2017189402 A1 | 11/2017 |

OTHER PUBLICATIONS

International Search Report and Written Opinion dated Oct. 23, 2018 for Application No. PCT/US2018/048748.
Maira Alejandra Garcia Jaramillo, "Prediction of postprandial blood glucose under intra-patent variabiity and uncertainty and its use in the design of insulin dosing strategies for type 1 diabetic patients", Jul. 22, 2011, pp. 1-178, Retrieved from the Internet: URL:http//dugi-doc.udg.edu/bitstream/handle/10256/4452/tmagj.pdf?sequene=1.

\* cited by examiner

US 11,715,553 B2

METHODS, DEVICES AND SYSTEMS FOR ESTIMATING NUTRITIONAL ELEMENT CONTENT IN FOODS

CROSS-REFERENCE TO RELATED APPLICATIONS

This disclosure is a national stage entry of and claims priority to International App. No. PCT/US2018/048748, filed Aug. 30, 2018, entitled "METHODS, DEVICES AND SYSTEMS FOR ESTIMATING NUTRITIONAL ELEMENT CONTENT IN FOODS," which claims priority to U.S. Provisional App. No. 62/552,587, filed Aug. 31, 2017 and entitled "METHODS, DEVICES AND SYSTEMS FOR ESTIMATING NUTRITIONAL ELEMENT CONTENT IN FOODS," the entireties of which are incorporated by reference herein.

TECHNICAL FIELD

This disclosure relates generally to mathematics, nutrition and medicine/medical diagnostics, and more particularly, it relates to improving nutritional element content estimates in foods via classifying or weighting individuals with a proficiency index.

BACKGROUND

Carbohydrate counting, also called "carb counting," is a meal planning tool for an individual with type 1 or type 2 diabetes. Carb counting includes tracking an amount of carbohydrate in foods eaten each day, which can be used to control the individual's blood glucose as carbohydrates affect blood glucose more than other nutritional elements in foods.

Carb counting can be performed by (1) knowing which foods to be eaten contain carbohydrates, (2) estimating a number of grams of carbohydrate in each food eaten, and (3) adding up the number of grams of carbohydrate from each food eaten to get a meal total or even a daily total. Through carb counting, the individual can better maintain blood glucose levels within a desired range, especially when used in conjunction with insulin therapy.

Unfortunately, nutritional element content can be quite difficult to estimate simply by viewing a food to be eaten. In fact, nutritional element content estimates by individuals typically show poor accuracy and reliability. See, e.g., Rusin et al. (2013) *Int. J. Med. Inform.* 82:653-664; and Rhyner et al. (2016) *J. Med. Internet Res.* 18:e101. To address this problem, computer vision systems for food recognition and nutritional element content estimates have been proposed, such as GoCARB™ (see, e.g., Rhyner et al. (2016)), which can be complex and can mischaracterize a food type.

Crowdsourcing, however, could be an effective alternative to provide greater accuracy and reliability of nutritional element content estimates in foods by individuals. For the foregoing reasons, there is a need for methods of estimating nutritional element content in foods via crowdsourcing, as well as devices and systems for the same.

BRIEF SUMMARY

In one embodiment, an improved graphical user interface (GUI) of a nutritional estimation tool is on an electronic device with a memory and one or more processors to execute one or more programs stored in the memory for determining a therapy or treatment based on a nutritional element content estimate and improving diabetes management, the improved GUI operatively coupled to the one or more processors. The improved GUI may include a therapy or treatment display based on at least one nutritional element content estimate and at least one proficiency index to improve accuracy and reliability when estimating nutritional element content in foods and therapy or treatment based therefrom.

The one or more processors may be adapted to execute computer implemented instructions to receive a plurality of nutritional element content estimates of a food image from a plurality of individuals correlated to a respective plurality of proficiency indexes. Each nutritional element content estimate from an individual may be correlated to a respective proficiency index for the individual corresponding to a pre-determined ability of the individual to accurately and reliably provide the nutritional element content estimate in the food image. The one or more processors may further be adapted to execute computer implemented instructions to calculate a weighted average of the nutritional element content estimates based on the respective plurality of proficiency indexes, display the weighted average on the improved GUI, and adjust the treatment or therapy display based on the weighted average.

The one or more processors may be adapted to execute computer implemented instructions to receive from an individual at least one nutritional element content estimate of a food image as a test, determine one or more deviation factors from the at least one nutritional element content estimate and a corresponding predetermined nutritional element content of the food image, assign the at least one proficiency index to the individual based upon the one or more deviation factors, and adjust the treatment or therapy display based on at least one nutritional element content estimate and at least one proficiency index.

In another embodiment, a method is provided of assigning to an individual a proficiency index for estimating nutritional element content of foods and utilizing the proficiency index to improve reliability and accuracy when estimating nutritional element content in foods and a therapy or treatment display based therefrom. The method may include displaying to the individual through a graphical user interface (GUI) a testing plurality of food images to test the individual on estimating nutritional element content in foods. Nutritional element content of one or more nutritional elements in each food image may be predetermined and not displayed. The method may further include receiving from the individual nutritional element content estimates of nutritional elements in the testing plurality of food images, determining one or more deviation factors from at least one nutritional element content estimate and a corresponding predetermined nutritional element content of the one or more nutritional elements in each food image, assigning the proficiency index of the individual based upon the one or more deviation factors, and adjusting a treatment or therapy display on the GUI for a food associated with a food image based on at least one nutritional element content estimate of the food image received from the individual and the proficiency index assigned to the individual.

A concept described herein includes "training followed by testing," which can be used to improve an individual's ability to estimate nutritional element content in foods. This concept can be achieved by using more than one plurality of food images to train and then test the individual's ability to estimate nutritional element content in foods. Based upon the training and testing, the individual is assigned a proficiency index that qualifies or quantifies the proficiency of the individual's estimates. Advantageously, the proficiency index can be used to weight future nutritional element content estimates by that individual. In this manner, a plurality of individuals having an assigned proficiency index can be used to increase accuracy and reliability of nutritional element content estimates in foods via crowdsourcing. This concept can be incorporated into exemplary methods, software/computer program products, devices and systems as described herein and in more detail below.

For example, methods are provided for assigning to an individual a proficiency index, where the proficiency index correlates to an ability to estimate nutritional element content in foods. One step includes displaying to the individual a first plurality of food images to thereby train the individual on estimating nutritional element content in foods, where nutritional element content of one or more nutritional elements in each food image is predetermined and is displayed with each food image. Another step includes displaying to the individual a second plurality of food images to thereby test the individual on estimating nutritional element content in foods, where nutritional element content of one or more nutritional elements in each food image is predetermined but is not displayed with each food image. Another step includes receiving or recording from the individual nutritional element content estimates on the second plurality of food images. Another step includes determining one or more deviation factors from at least one received/recorded nutritional element content estimate and the at least one corresponding predetermined nutritional element content for one or more of the second plurality of food images and then assigning the proficiency index to the individual based upon the one or more deviation factors.

Alternate methods are provided for assigning to an individual a proficiency index, where the proficiency index correlates to an ability to estimate nutritional element content in foods. One step includes displaying to the individual a first plurality of food images to train the individual on estimating nutritional element content in foods, where nutritional element content of one or more nutritional elements in each food image is predetermined and is not displayed with each food image. Another step includes receiving or recording from the individual nutritional element content estimates on the first plurality of food images. Another step includes providing to the individual the predetermined nutritional element contents of the first plurality of food images to permit learning or correcting. Another step includes displaying to the individual a second plurality of food images to test the individual on estimating nutritional element content in foods, where nutritional element content of one or more nutritional elements in each food image is predetermined and is not displayed with each food image. Another step includes receiving or recording from the individual nutritional element content estimates on the second plurality of food images. Another step includes determining one or more deviation factors from at least one received/recorded nutritional element content estimate and the corresponding predetermined nutritional element for one or more of the second plurality of food images and then assigning the proficiency index to the individual based upon the one or more deviation factors.

In some instances, and when an individual already has experience in providing nutritional element content estimates, the training steps can be optional or even omitted and the individual simply can be shown the second plurality of food images and tested accordingly to determine one or more deviation factors and ultimately assign the proficiency index.

In some instances of the above methods, the first and/or the second plurality of food images are manually displayed to the individual. In other instances, the first and/or the second plurality of food images are electronically displayed to the individual on, for example, a display of a mobile device, a tablet or a computer. As such, the methods can be manually implemented or can be partially or wholly computer implemented. In certain instances, the methods are used in connection with networked mobile computing devices adapted with applications/software/computer program products that incorporate the methods described herein.

In some instances, the nutritional elements can be calories, carbohydrates, fats and proteins. In other instances, the nutritional element can be calories, carbohydrates and fats; calories, carbohydrates and proteins; calories, fats and proteins; or carbohydrates, fats and proteins. In other instances, the nutritional elements can be calories and carbohydrates; calories and fats; calories and proteins; carbohydrates and fats; carbohydrates and proteins; or fats and proteins. In still other instances, the nutritional element can be calories or carbohydrates or fats or proteins, particularly carbohydrates.

In some instances, the proficiency index is a qualitative proficiency index. For example, the proficiency index can be a level of expertise such as, for example, an expert estimator, an experienced estimator, or a beginner estimator. In particular instances, the qualitative proficiency index is based upon the deviation factor, where the deviation factor for the expert estimator is 0-10, the deviation factor for the experienced estimator is 11-50, and the deviation factor for the beginner estimator is 51 and above.

In other instances, the proficiency index is a quantitative proficiency index. For example, the proficiency index can be an expertness quotient (EQ) that is calculated from a deviation of the individual's nutritional element content estimate and predetermined content for each food image (or meal) M according to the following for N individuals:

$$EQ_j = 1 / \sqrt{\frac{1}{M} \sum_{i=1}^{M} \left( \frac{100(c_{ij} - c_i)}{c_i} \right)^2 }, j = 1, 2, \ldots, N. \qquad \text{(Equation 1)}$$

Alternatively, the proficiency index for the individual can be calculated based upon an average of selected M estimates, a median of the M estimates, a mode of the M estimates, and a weighted average of the M estimates.

In some instances, the methods further include a step of re-testing and re-assigning the proficiency index of the individual after a predetermined period of time by repeating the assigning methods described herein. In other instances, the re-testing and re-assigning of the proficiency index can be randomly repeated.

Also provided herein are methods of estimating nutritional element content in a food by a plurality of individuals, such as by crowdsourcing. One step includes displaying a food image to each of the plurality of individuals, where each of the plurality of individuals has an assigned proficiency index that correlates to an ability to estimate nutritional element content in foods, and where the proficiency index is assigned according to the assigning methods described herein. Another step includes receiving or recording from each of the plurality of individuals the nutritional element content estimate in the food image and then calculating and displaying to a requestor a weighted average of the received nutritional element content estimates. An optional step includes adjusting a treatment or therapy for a disease or disorder, such as increasing or decreasing an insulin dose or other medicine, based upon the weighted average.

Alternate methods are provided for determining a weighted average of nutritional element content estimates in a food image. One step includes receiving a food image from a requestor on a primary device. Another step includes electronically displaying the food image to a plurality of individuals on a plurality of secondary devices, wherein each of the plurality of individuals has a proficiency index assigned according to the assigning methods described herein. Another step includes receiving via wired or wireless means from the plurality of individuals their nutritional element content estimate in the food image and automatically calculating a weighted average of the received nutritional element content estimates. Another step includes electronically displaying the weighted average of the nutritional element content estimates to the requestor on the primary device. An optional step includes adjusting a treatment or therapy for a disease or disorder, such as increasing or decreasing an insulin dose or other medicine, based upon the weighted average.

In some instances of the above methods, the weighted average of the nutritional element content estimates is from a minimum of N individuals. In certain instances, the minimum of N individuals can be about 5 individuals, about 10 individuals, about 15 individuals, about 20 individuals, about 25 individuals or even about 30 individuals.

In some instances, the methods also include selecting only those nutritional element content estimates from individuals within the plurality of individuals having the assigned proficiency index above a predetermined threshold and then calculating and displaying to the requestor a weighted average of the selected nutritional element content estimates. The selecting can include a minimum number of individuals having the assigned proficiency index above a predetermined threshold (i.e., fewer, more proficient individuals may be needed to meet the threshold, or more, less proficient individuals may be needed to meet the threshold).

In some instances, the methods also include a step of providing the weighted average together with a confidence indicator to convey an expected accuracy and/or reliability of the weighted average of the nutritional element content estimates.

In some instances, the methods further include a step of re-testing and re-assigning the proficiency index of one or more individuals after a predetermined period of time by repeating the assigning methods described herein. In other instances, the re-testing and re-assigning of the proficiency index can be randomly repeated.

In some instances, the methods are wholly or partially computer implemented.

In view of the above, software such as computer-readable media/computer program products are provided that are configured to include computer-executable instructions for performing one or more of the methods as described herein.

Likewise, devices and systems are provided that are configured to carry out one or more of the methods as described herein. In some instances, the devices and systems can include at least a processor, a memory, and/or a transceiver, where the processor is configured to execute one or more of the methods as described herein.

These and other advantages, effects, features and objects of the concept will become better understood from the description that follows. The description of exemplary embodiments is not intended to limit the concept to the particular forms disclosed, but on the contrary, the intention is to cover all modifications, equivalents and alternatives falling within the spirit and scope of the concept as defined by the embodiments above and the claims below. Reference should therefore be made to the embodiments above and claims below for interpreting the scope of the concept.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DESCRIPTION OF EXEMPLARY EMBODIMENTS

Figure 1:
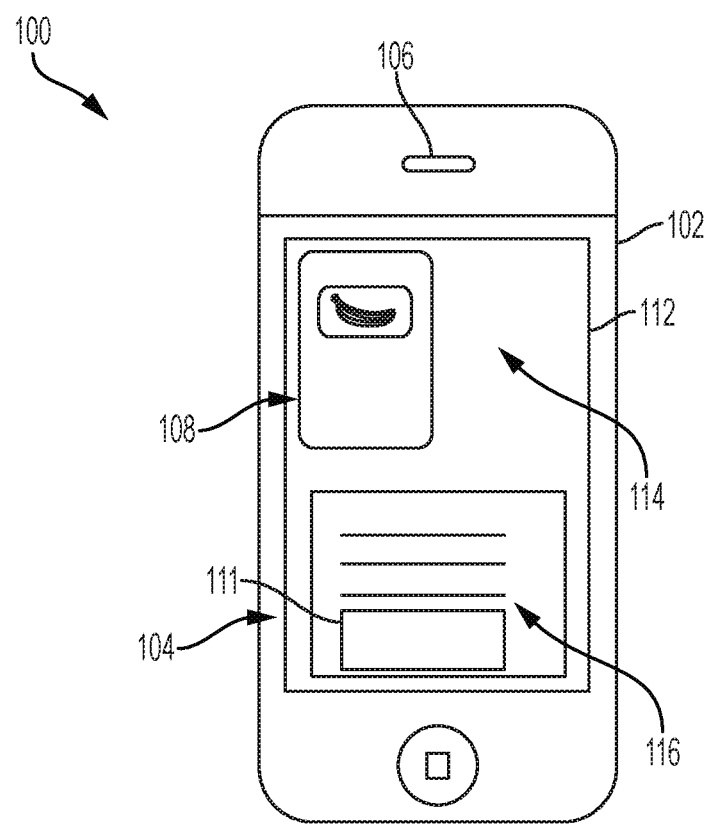
FIG. 1 schematically illustrates a device system for adjusting a therapy or treatment display based on at least one proficiency index, according to one or more embodiments as shown and described herein.

The methods, software/computer program products, devices and systems now will be described more fully hereinafter. Indeed, the methods, software/computer program products, devices and systems may be embodied in many different forms and should not be construed as limited to the embodiments set forth herein; rather, these embodiments are provided so that this disclosure will satisfy applicable legal requirements.

Likewise, many modifications and other embodiments of the methods, software/computer program products, devices and systems described herein will come to mind to one of skill in the art to which the disclosure pertains having the benefit of the teachings presented in the foregoing descriptions and the associated drawings. Therefore, it is to be understood that the methods, software/computer program products, devices and systems are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

The methods, software/computer program products, devices and systems described herein incorporate the "training followed by testing" concept, which can be used to improve an individual's accuracy and reliability in estimating an amount or content of an element or component in a complex composition or mixture. The methods, software/computer program products, devices and systems therefore are useful in a variety of applications. For example, "training followed by testing" can be used to improve accuracy and reliability in estimating content of one or more nutritional elements in foods, which is important in managing diseases such as diabetes, heart disease, metabolic syndrome, or obesity. In fact, an accurate and reliable carbohydrate content estimate from a food can be used to adjust a treatment or therapy for managing diabetes, such as adjusting a bolus amount of insulin to be administered to an individual. Moreover, the methods can be used to further improve accuracy and reliability when estimating nutritional element content in foods via crowdsourcing.

As used herein, "nutritional element" or "nutritional elements" means one or more of the components that make up a food such as its calories, carbohydrates, fats, fiber, minerals, proteins, servings, vitamins, and/or water.

Likewise, and as used herein, "nutritional element content estimate" or "nutritional element content estimates" means an assessment, such as an educated guess, of an amount or content of one or more nutritional elements in a food. For example, and with respect to carbohydrates, a nutritional element content estimate would be an amount or content of carbohydrate in a food in grams.

While the methods, software/computer program products, devices and systems described herein use carbohydrate counting as an example, they are not intended to be limited strictly to medical applications. In fact, it is contemplated that "training followed by testing" could be readily adapted to environmental applications by estimating amounts of components in soil samples or liquid samples. Alternatively, "training followed by testing" could be readily adapted to athletic applications, especially for athletic training or for building and maintaining muscle or for lowering body fat, by estimating calories and/or nutritional element content. Alternatively still, "training followed by testing" could be readily adapted to nutritional applications, especially for weight loss or lowering blood cholesterol.

As such, a technical effect of the methods, software/computer program products, devices and systems described herein is that nutritional element content estimates can be rendered more accurately and reliably than when made without "training followed by testing," which as noted above, is particularly advantageous when adjusting and/or making treatment or therapy decisions.

Methods

The methods herein include steps that may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps.

Part of the "training followed by testing" concept includes assigning to an individual a proficiency index that correlates to the individual's ability to accurately and reliably estimate nutritional element content in foods. As such, methods are provided for initially assigning to an individual a proficiency index, as well as for updating the individual's proficiency index.

In general, the methods can begin by selecting an individual (or more) for training followed by testing. With respect to carbohydrate counting, exemplary individuals include, but are not limited to, individuals with diabetes or caregivers for individuals with diabetes. Other exemplary individuals include athletes, chefs, dieticians, nurses, physicians and trainers.

Once the individual is selected, the methods can include displaying to the individual a first plurality of food images to thereby train the individual on estimating nutritional element content in foods. The nutritional element content of one or more nutritional elements in each food image of the first plurality of food images is known/predetermined and is displayed or provided to the individual during the training.

In some instances, the nutritional elements that are known for each food image of the first plurality of food images are calories, carbohydrates, fats and proteins. In other instances, the nutritional elements that can be known for each food image of the first plurality of food images can be calories, carbohydrates and fats; calories, carbohydrates and proteins; calories, fats and proteins; or carbohydrates, fats and proteins. In other instances, the nutritional elements that are known for each food image of the first plurality of food images can be calories and carbohydrates; calories and fats; calories and proteins; carbohydrates and fats; carbohydrates and proteins; or fats and proteins. In still other instances, the nutritional elements that are known for each food image of the first plurality of food images can be calories or carbohydrates or fats or proteins. Thus, at least one nutritional element content is known for each food image such as, for example, an amount of calories, an amount of carbohydrates in grams, an amount of fats in grams, and/or an amount of protein in grams. Here, the at least one nutritional element content that is known for each food image is carbohydrates in grams.

Each of the food images in the first plurality of food images can be automatically displayed to the individual for a predetermined period of time such as, for example, from about 5 seconds to about 60 seconds, for about 10 seconds to about 55 seconds, for about 15 seconds to about 50 seconds, for about 20 seconds to about 45 seconds, for about 25 seconds to about 40 seconds, or even for about 30 seconds to about 35 seconds. In some instances, each food image can be displayed for about 5 seconds, for about 10 seconds, for about 15 seconds, for about 20 seconds, for about 25 seconds, for about 30 seconds, for about 35 seconds, for about 40 seconds, for about 45 seconds, for about 50 seconds, for about 55 seconds, or even for about 60 seconds. In other instances, each food image can be displayed for more than 60 seconds. Here, each food image in the first plurality of food images is displayed to the individual for less than 60 seconds.

Alternatively, each of the food images in the first plurality of food images (and predetermined nutritional element content) can be manually advanced such as by input from the individual and therefore displayed for a period of time selected by the individual. There can, however, be a maximum time for which each food image is displayed before the next image is displayed if there is no input from the individual such as, for example, for about 5 seconds, for about 10 seconds, for about 15 seconds, for about 20 seconds, for about 25 seconds, for about 30 seconds, for about 35 seconds, for about 40 seconds, for about 45 second, for about 50 seconds, for about 55 seconds, or even for about 60 seconds. In other instances, the maximum display time can be more than 60 seconds. Here, the maximum display time is about 60 seconds.

In some instances, a time clock can be displayed with each image to thereby show the individual how much time remains for making a nutritional element content estimate.

As used herein, "about" means within a statistically meaningful range of a value or values including, but not limited to, a stated amount, concentration, content, length, width, height, angle, weight, molecular weight, pH, sequence identity, time frame, temperature or volume. Such a value or range can be within an order of magnitude, typically within 20%, more typically within 10%, and even more typically within 5% of a given value or range. The allowable variation encompassed by "about" can be readily appreciated by one of skill in the art.

Generally, the nutritional element content is simultaneously displayed when each food image is displayed. Alternatively, however, there can be a delay between when each food image is displayed and when the nutritional element content is then displayed for the food image. In some instances, the delay between when each food image is displayed and when the nutritional element content is then displayed can be for about 1 second to about 10 seconds, for about 2 seconds to about 9 seconds, for about 3 seconds to about 8 seconds, for about 4 seconds to about 7 seconds, or for about 5 seconds to about 6 seconds. In other instances, the delay between when each food image is displayed and when the nutritional element content is then displayed can be for about 1 second, for about 2 seconds, for about 3 seconds, for about 4 seconds, for about 5 seconds, for about 6 seconds, for about 7 seconds, for about 8 seconds, for about 9 seconds, or even for about 10 seconds. In still other instances, the delay can be for more than 10 seconds such as, for example, for about 15 seconds, for about 20 seconds, for about 25 seconds, or even for about 30 seconds. In further instances, the delay between when each food image is displayed and when the nutritional element content is then displayed can be less than 60 seconds. Here, the delay is at least for about 15 seconds. Regardless of the length of the delay, it is contemplated that the individual can override the delay if the time has not lapsed if the individual is ready to view the nutritional element content and advance to the next image.

In yet another form, the nutritional element content for each image of the first plurality of food images is not displayed/provided to the individual until after all of the images have been displayed. In some instances, both the estimated and the actual nutritional element contents can be displayed. In still other instances, additional information also can be displayed including, but not limited to, an assessment of nutritional element type (e.g., with respect to carbohydrates, the assessment can be a low, mid or high glycemic content).

The first plurality of food images can include from about 5 food images to about 50 food images, from about 10 food images to about 45 food images, from about 15 food images to about 40 food images, from about 20 food images to about 35 food images, or from about 25 food images to about 30 food images. In some instances, the first plurality of food images can include about 5 food images, about 10 food images, about 15 food images, about 20 food images, about 25 food images, about 30 food images, about 35 food images, about 40 food images, about 45 food images, or even about 50 food images. Alternatively, the first plurality of food images can be less than 50 food images. In further instances, the first plurality of food images can include more than 50 food images such as, for example, about 55 food images, about 60 food images, about 65 food images, about 70 food images, about 75 food images, about 80 food images, about 85 food images, about 90 food images, about 95 food images, or even about 100 food images. Here, the first plurality of food images is about 25 food images.

In the methods, the first plurality of food images therefore can be manually/physically displayed to the individual, electronically displayed to the individual, or a combination of both.

Once the training step is completed, the methods can proceed to a testing step, which can include displaying to the individual a second plurality of food images to thereby test the individual on estimating nutritional element content in foods. As above, the nutritional element content of one or more nutritional elements in each food image of the second plurality of food images is known/predetermined. However, in contrast to above, the nutritional element content is not displayed or provided to the individual during the testing.

In some instances, however, the training steps can be optional or even omitted and the individual simply can be shown the second plurality of food images and tested accordingly. Examples of when the training step can be optional/omitted include, but are not limited to, when an individual already has experience in providing nutritional element content estimates.

As above, the nutritional elements that are known for each food image of the second plurality of food images are calories, carbohydrates, fats and proteins. In other instances, the nutritional elements that are known for each food image of the second plurality of food images can be calories, carbohydrates and fats; calories, carbohydrates and proteins; calories, fats and proteins; or carbohydrates, fats and proteins. In other instances, the nutritional elements that are known for each food image of the second plurality of food images can be calories and carbohydrates; calories and fats; calories and proteins; carbohydrates and fats; carbohydrates and proteins; or fats and proteins. In still other instances, the nutritional elements that are known for each food image of the second plurality of food images can be calories or carbohydrates or fats or proteins. Thus, at least one nutritional element content is known for each food image such as, for example, an amount of carbohydrates in grams, an amount of fats in grams, and/or an amount of protein in grams. Here, the at least one nutritional element content that is known for each food image is carbohydrates in grams.

Like the first plurality of food images, each of the food images in the second plurality of food images can be displayed to the individual for a predetermined period of time such as, for example, for about 5 seconds to about 60 seconds, for about 10 seconds to about 55 seconds, for about 15 seconds to about 50 seconds, for about 20 seconds to about 45 seconds, for about 25 seconds to about 40 seconds, or even for about 30 seconds to about 35 seconds. In some instances, each food image can be displayed for about 5 seconds, for about 10 seconds, for about 15 seconds, for about 20 seconds, for about 25 seconds, for about 30 seconds, for about 35 seconds, for about 40 seconds, for about 45 seconds, for about 50 seconds, for about 55 seconds, or even for about 60 seconds. In other instances, each food image can be displayed for more than 60 seconds. Here, each food image in the second plurality of food images is displayed to the individual for less than 60 seconds.

Also like the first plurality of food images, the second plurality of food images can include from about 5 food images to about 50 food images, from about 10 food images to about 45 food images, from about 15 food images to about 40 food images, from about 20 food images to about 35 food images, or from about 25 food images to about 30 food images. In some instances, the second plurality of food images can include about 5 food images, about 10 food images, about 15 food images, about 20 food images, about 25 food images, about 30 food images, about 35 food images, about 40 food images, about 45 food images, or even about 50 food images. Alternatively, the second plurality of food images can be less than 50 food images. In further instances, the second plurality of food images can include more than 50 food images such as, for example, about 55 food images, about 60 food images, about 65 food images, about 70 food images, about 75 food images, about 80 food images, about 85 food images, about 90 food images, about 95 food images, or even about 100 food images. Here, the second plurality of food images is about 25 food images.

It is contemplated that the first plurality of food images and the second plurality of food images can include the same number of food images; however, the number of food images in the first plurality of food images and the second plurality of food images can be different from one another.

In the methods, the second plurality of food images therefore can be manually/physically displayed to the individual, electronically displayed to the individual, or a combination of both.

During the testing, nutritional element content estimates from one or more of the food images in the second plurality of food images are received or recorded from the individual. From the received nutritional element content estimates, one or more deviation factors are calculated from a difference between at least one received/recorded nutritional element content estimate and the at least one corresponding predetermined nutritional element content for one or more of the second plurality of food images.

To further refine the individual's ability to estimate nutritional element content in foods, it is contemplated that the known/predetermined nutritional element content for each image of the second plurality of food images can be displayed/provided to the individual after all of the images have been displayed (i.e., the testing is complete and all the individual's nutritional element content estimates have been received/recorded).

Once the testing step is completed, the methods can proceed to an assigning step, which can include using the one or more of the deviation factors to determine and then assign to the individual a proficiency index. In some instances, the proficiency index is a qualitative proficiency index. For example, the proficiency index can be a level of expertise such as, for example, an expert estimator, an experienced estimator, or a beginner estimator. In particular instances, the deviation factor for the expert estimator is 0-10, the deviation factor for the experienced estimator is 11-50, and the deviation factor for the beginner estimator is 51 and above.

In other instances, the proficiency index is a quantitative proficiency index. For example, the proficiency index can be an EQ. In some instances, the EQ is calculated based off of a deviation of the individual's nutritional element content estimate and known/predetermined nutritional element content for each food (or meal) image M according to the following for N individuals, where $C_{ij}$ is the nutritional element content estimate and $C_i$ is the predetermined nutritional element content, respectively:

$$EQ_j = 1/\sqrt{\frac{1}{M}\sum_{i=1}^{M}\left(\frac{100(c_{ij}-c_i)}{c_i}\right)^2}, j = 1, 2, \ldots, N. \quad \text{(Equation 1)}$$

In this case, the proficiency index is an expertness quotient or "EQ."

Alternatively, the proficiency index for the individual can be calculated based upon an average of the M estimates, a median of the M estimates, a mode of the M estimates, and a weighted average of the M estimates, where the weights are obtained differently than as in the EQ.

Because the individual will continue to gain experience in estimating nutritional element contents, the methods include re-testing and re-assigning the individual's proficiency index after a predetermined period of time by repeating the assigning methods above. Alternatively, the re-testing and re-assigning can occur randomly.

The above methods are particularly advantageous after a number of individuals have been assigned a proficiency index and are enlisted to estimate nutritional element content in a food displayed by a requestor. As used herein, "requestor" means an individual in need of a nutritional element content estimate in a food, especially a crowdsourced nutritional element content. Crowdsourced nutritional element content estimates, especially carbohydrate content estimates, advantageously can be used to control blood glucose levels, as well as can be used when adjusting a treatment or therapy such as calculating a bolus insulin dose to be administered to the individual.

In view thereof, methods also are provided for accurately and reliably estimating nutritional element content in a food via crowdsourcing. In general, the methods can begin by providing a plurality of individuals having an assigned proficiency index, where the proficiency index is determined and assigned according to the assigning methods described herein.

With respect to estimating carbohydrate content, exemplary individuals include, but are not limited to, individuals with diabetes or caregivers for individuals with diabetes. Other exemplary individuals include athletes, chefs, dieticians, nurses, physicians and trainers.

Once the plurality of individuals is determined, the methods can proceed to a displaying step, where an image by a requestor, such as an image of a food (or meal), is displayed to each of a plurality of individuals. As used herein, "requestor" means an individual wishing to obtain a crowdsourced nutritional element content, such as carbohydrate content, of a food.

After displaying the food image, the methods can proceed to a receiving step in which nutritional element content estimates on the food image are received or recorded from each of the plurality of individuals. Optionally, the receiving step also can include selecting nutritional element content estimates only from those individuals having the assigned proficiency index above a predetermined threshold. For example, and with respect to individuals assigned a qualitative proficiency index, the predetermined threshold can be individuals assigned to be at least an experienced estimator.

Once the receiving and optional selecting steps are completed, the methods can proceed to a calculating and displaying step, in which the requestor is shown a weighted average of the received and/or selected nutritional element content estimates. In some instances, the weighted average is from a minimum of N individuals such as, for example, 5 individuals, 10 individuals, 15 individuals, 20 individuals, 25 individuals, 30 individuals, 35 individuals, 40 individuals, 45 individuals, or even 50 individuals. In other instances, the minimum of N individuals is less than 500 individuals, less than 400 individuals, less than 300 individuals, less than 200 individuals, or even less than 100 individuals. In still other instances, the minimum of N individuals is more than 500 individuals. In particular instances, the minimum of N individuals is between about 20 individuals to about 40 individuals, especially 30 individuals. In some instances, the weighted average is provided together with a confidence indicator to convey the expected reliability of the nutritional element content estimate.

In an alternative form, methods are provided for determining a weighted average of nutritional element content estimates in a food image, such as crowdsourced nutritional element content estimates. One step includes receiving a food image from a requestor on a primary device. Another step includes electronically displaying the food image to a plurality of individuals on a plurality of secondary devices, wherein each of the plurality of individuals has a proficiency index assigned according to the assigning methods described herein. Another step includes receiving via wired or wireless means from the plurality of individuals their nutritional element content estimate in the food image and automatically calculating a weighted average of the received nutritional element content estimates. Another step includes electronically displaying the weighted average of the nutritional element content estimates to the requestor on the primary device. An optional step includes adjusting a treatment or therapy for a disease or disorder, such as increasing or decreasing an insulin dose or other medicine, based upon the weighted average.

To account for on-going improvement in an individual's ability to estimate nutritional element content and to further improve the accuracy and reliability of crowdsourced estimates, the above methods optionally can include a re-testing and re-assigning step, in which the proficiency index of the individual is updated by repeating the assigning methods described herein after a predetermined period of time. In some instances, the predetermined period of time can be within a day or two, with a week, or even with a month from which the proficiency index was initially assigned. Alternatively, the re-testing and re-assigning step can be randomly repeated.

Another option to account for on-going improvement in an individual's ability to estimate nutritional element content, the proficiency index of the individual can be updated based upon how close the individual's nutritional element content estimates are to community-weighted averages over a predetermined number of previous estimates. For example, another deviation quotient can be calculated. Alternatively, the proficiency index of the individual can be updated based upon a running average of the previous X estimates for that individual. In some instances, the predetermined number of previous estimates can about from about 5 estimates to about 50 estimates, from about 10 estimates to about 45 estimates, from about 15 estimates to about 40 estimates, from about 20 estimates to about 35 estimates, or about 25 estimates to about 30 estimates. In other instances, the predetermined number of previous estimates can be about 5 estimates, about 10 estimates, about 15 estimates, about 20 estimates, about 25 estimates or even about 30 estimates. In still other instances, the proficiency index of the individual can be updated based upon a running average of the individual's previous proficiency indices.

To further provide more accurate and reliable nutritional element content estimates, the plurality of individuals can be further limited by selecting individuals having certain demographic characteristics that may influence their ability to assess nutritional element content. For example, individuals of a particular ethnic group may be preferred when assessing carbohydrate content in a food originating with that particular ethnic group. Likewise, individuals having a history of accurately and reliably providing a nutritional element content estimate for a particular food type (i.e., having a high proficiency index for that food type) may be preferred when assessing carbohydrate content in that food type. Other examples include selecting individuals having a particular disease or disorder (e.g., Type 1 vs Type 2 diabetic; gluten intolerant, lactose intolerant, etc.), having a particular location/geography in which they are familiar with or reside, or having a predetermined number of years estimating nutritional element contents.

Accuracy and reliability of an individual to provide nutritional element content estimates also can be improved by displaying food types that the individual consistently overestimates or underestimates during the re-testing and re-assigning step.

In some instances, the above methods are wholly or partially computer implemented. In such computer-implemented instances, individual and requestor demographics, qualifications, food images and associated community estimations may be stored on a remote server. Furthermore, food images and estimates collected with these methods may be used to train artificial neural networks or other machine learning networks to, overtime, complement or substitute for crowdsourced nutritional estimations.

In summary, the methods described herein can be used to improve the accuracy and precision of crowdsourced nutritional element content estimates by qualifying or quantifying an individual's experience into a proficiency index and then weighting their estimations according to the proficiency index. The crowdsourced nutritional element content estimates, especially carbohydrate content, are particularly important with respect to determining or adjusting a treatment or a therapy such as insulin bolus doses. When determining or adjusting insulin bolus doses, it may be advantageous to select the most proficient individuals, such as the individuals in the top 5%, top 10%, or even top 15% of individuals.

Software

It is expected that one of skill in the art, notwithstanding possibly significant effort and many design choices motivated by, for example, available time, current technology, and economic considerations, when guided by the concept and principles disclosed herein will be readily capable of generating applications, software instructions and/or computer program products based upon the methods described above with minimal experimentation.

In view thereof, the methods described above may be implemented using computer programming or engineering techniques including software such as applications, computer-readable media, computer program products, firmware, hardware or any combination or subset thereof. Any such resulting application, media or computer program, having computer-readable code means, may be embodied or provided within one or more non-transitory computer-readable media, thereby making the software or computer program product (i.e., an article of manufacture).

As used herein, "software," "computer-readable media" or "computer program product" means one or more organized collections of computer data and instructions, which can be divided into two major categories, system software and application software. System software interfaces with hardware, and application software interfaces with a user. Moreover, system software includes the operating system software and firmware, as well as any middleware and drivers installed in a system. The system software provides the basic non-task-specific functions of the computer. In contrast, the application software is used to accomplish specific tasks.

Exemplary computer-readable media include, but are not limited to, a flash memory drive, digital versatile disc (DVD), compact disc (CD), fixed (hard) drive, diskette, optical disk, magnetic tape, semiconductor memory such as read-only memory (ROM), and/or any transmitting/receiving medium such as the Internet or other communication network or link. By way of example and not limitation, computer-readable media includes computer-readable storage media and communication media. Computer-readable storage media are tangible and non-transitory and store information such as computer-readable instructions, data structures, program modules, and other data. Communication media, in contrast, typically embody computer-readable instructions, data structures, program modules, or other data in a transitory modulated signal such as a carrier wave or other transport mechanism and include any information delivery media. Combinations of any of the above also are included within the scope of computer-readable media. The article of manufacture containing the computer code may be made and/or used by executing the code directly from one medium, by copying the code from one medium to another medium, or by transmitting the code over a network.

In view thereof, the computer-readable media/computer program products can include a number of modules configured/programmed for performing the methods described herein.

In some instances, non-transitory computer-readable media or computer program products are provided that include instructions for causing an electronic device such as a handheld electronic device or a computer to execute a method that includes a step of displaying to an individual a first plurality of food images to train the individual on estimating nutritional element content in foods, where nutritional element content of one or more nutritional elements in each food image is predetermined and displayed.

The non-transitory computer-readable media or computer program products also can include instructions for executing a step of displaying to the individual a second plurality of food images to test the individual on estimating nutritional element content in foods, where nutritional element content of one or more nutritional elements in each food image is predetermined and not displayed.

The non-transitory computer-readable media or computer program products further can execute a step of receiving from the individual nutritional element content estimates of nutritional elements in the second plurality of food images.

The non-transitory computer-readable media or computer program products further can include instructions for executing a step of determining one or more deviation factors from at least one nutritional element content estimate and the individual to a corresponding predetermined nutritional element content of the one or more nutritional elements in each food image and assigning the proficiency index of the individual based upon the one or more deviation factors.

In other instances, non-transitory computer-readable media or computer program products are provided that include instructions for causing an electronic device such as a handheld electronic device or a computer to execute a method that includes a step of displaying to an individual a first plurality of food images to train the individual on estimating nutritional element content in foods, where nutritional element content of one or more nutritional elements in each food image is predetermined and not displayed.

The non-transitory computer-readable media or computer program products also can include instructions for executing a step of receiving or recording from the individual nutritional element content estimates of the first plurality of food images.

The non-transitory computer-readable media or computer program products further can include instructions for executing a step of providing to the individual the predetermined nutritional element content of the one or more nutritional elements in the first plurality of food images to permit learning or correcting.

The non-transitory computer-readable media or computer program products further can include instructions for executing a step of displaying to the individual a second plurality of food images to test the individual on estimating nutritional element content in foods, where nutritional element content of one or more nutritional elements in each food image is predetermined but not displayed.

The non-transitory computer-readable media or computer program products further can include instructions for executing a step of receiving from the individual nutritional element content estimates of nutritional elements in the second plurality of food images.

The non-transitory computer-readable media or computer program products further can include instructions for executing a step of determining one or more deviation factors from at least one nutritional element content estimate and the individual to a corresponding predetermined nutritional element content of the one or more nutritional elements in each food image and assigning the proficiency index of the individual based upon the one or more deviation factors.

In still other instances, non-transitory computer-readable media or computer program products are provided that include instructions for causing an electronic device such as a handheld electronic device or a computer to execute a method that includes a step of displaying a food image to a plurality of individuals, where each of the plurality of individuals has a proficiency index that correlates to an ability to provide a nutritional element content estimate in the food image, and wherein the proficiency index is assigned according to the assigning methods described herein.

The non-transitory computer-readable media or computer program products also can include instructions for executing a step of receiving from each of the plurality of individuals the nutritional element content estimate in the food image.

The non-transitory computer-readable media or computer program products further can include instructions for executing a step of calculating and displaying a weighted average of the nutritional element content estimates.

Devices and Systems

Devices are provided that are configured for assigning to an individual a proficiency index for classification. Additionally or alternatively, the devices can be configured for estimating nutritional element content of foods, especially via crowdsourcing.

Regardless of its intended use, the devices can include one or more of the following: a housing, a display, an input/output peripheral, a memory, a processor, a power source, a user interface, a storage device, a wired and/or wireless communication means.

As used herein, "processor" mean central processing units, microprocessors, microcontrollers, reduced instruction circuits (RISC), application specific integrated circuits (ASIC), logic circuits, and any other circuit or processor capable of executing the functions/methods described herein. Regardless of the type of processor, it is configured to execute one or more of the methods described herein.

Exemplary devices include, but are not limited to, computers and laptops, portable computing devices such as mobile devices (e.g., handheld gaming consoles, smartphones, smart watches and tablets), and test meters such as blood glucose test meters.

FIG. 1 schematically illustrates an embodiment of a device system 100 for adjusting a therapy or treatment display based on at least one proficiency index. The device system 100 includes a device 102 that may be a smart mobile device including a display screen 104 and a camera 106. The display screen 104 may further include a food image 108. In embodiments, the device 102 may be or be communicatively coupled to a medical device that may be a blood glucose meter, a continuous glucose monitor, an insulin pump, an insulin, a wellness device, or a like medical device.

A nutritional estimation tool 112 on the device 102 configured to assign and/or provide at least one proficiency index 111 and a therapy or treatment display 116 based on at least one proficiency index 111 on a GUI 114 of the nutritional estimation tool 112 as shown on the display screen 104. The nutritional estimation tool 112 is configured to executed logic to implement the methods as described herein.

Figure 2:
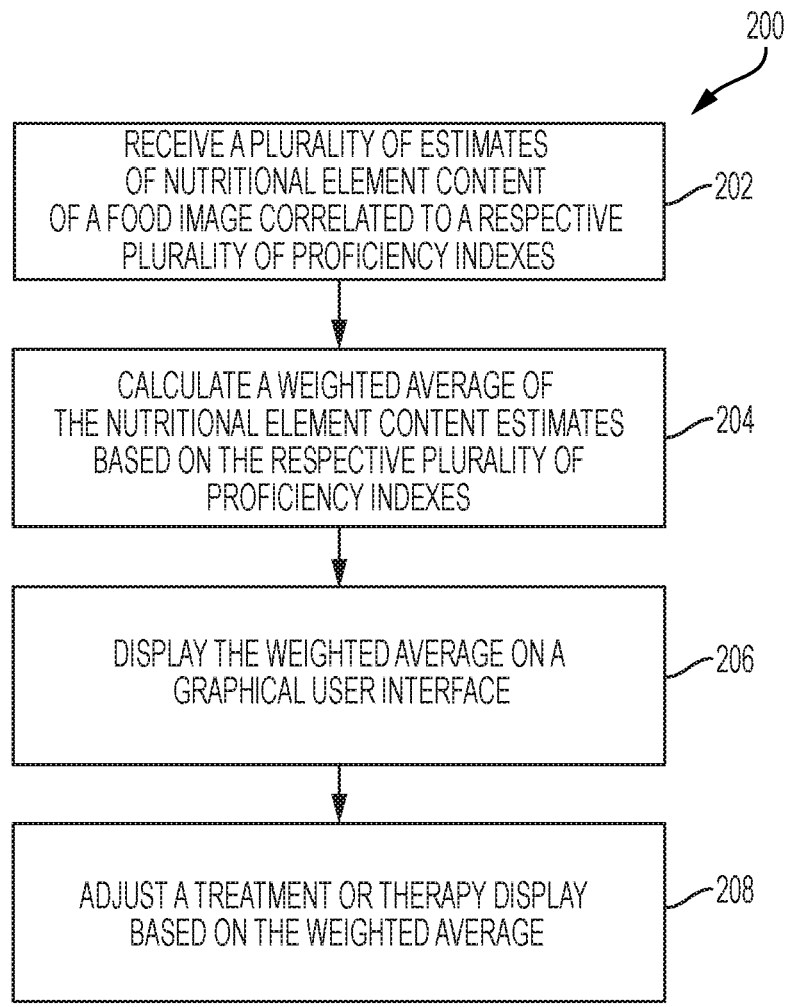
FIG. 2 schematically illustrates a process outlining steps to determine and display a weighted average based on a plurality of proficiency indexes to adjust a therapy or treatment display, according to one or more embodiments as shown and described herein.

As a non-limiting example, referring to FIG. 2, a method 200 may follow logic to, in block 202, receive a plurality of nutritional element content estimates of a food image 108 from a plurality of individuals correlated to a respective plurality of proficiency indexes 111. Each nutritional element content estimate from an individual may be correlated to a respective proficiency index for the individual corresponding to a pre-determined ability of the individual to accurately and reliably provide the nutritional element content estimate in the food image 108. In block 204, the method 200 may follow logic to calculate a weighted average of the nutritional element content estimates based on the respective plurality of proficiency indexes 111. In block 206, the method 200 may follow logic to display the weighted average on the improved GUI 114, and, in block 208, to adjust the treatment or therapy display 116 based on the weighted average.

Figure 3:
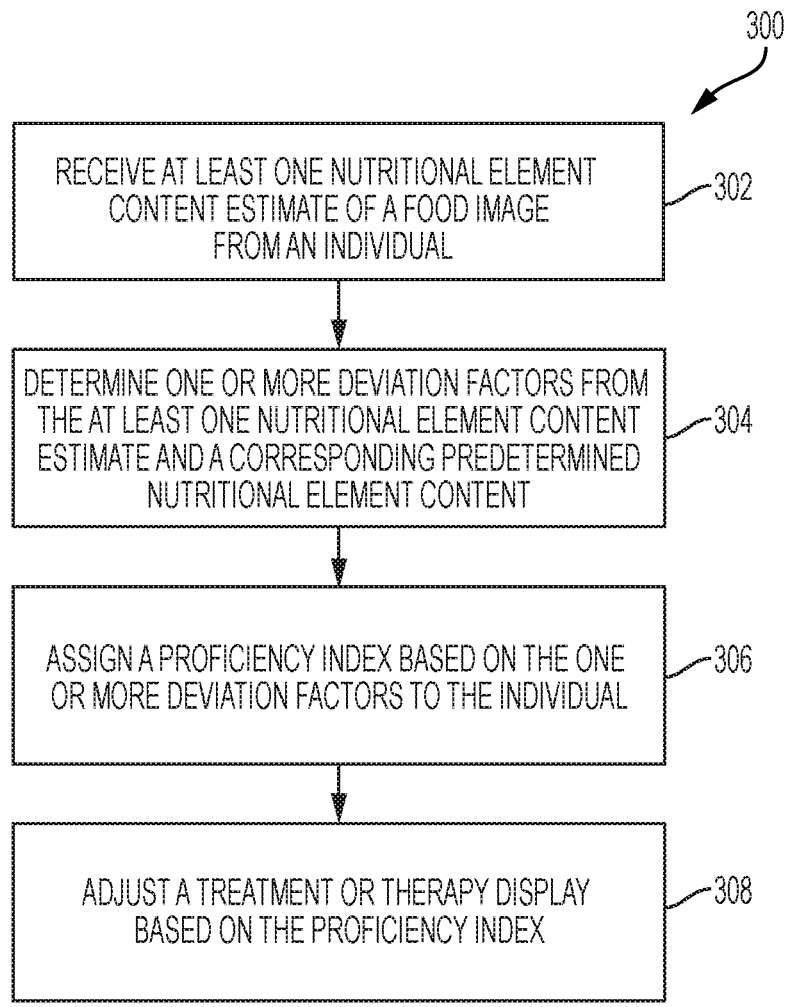
FIG. 3 schematically illustrates a process outlining steps to determine and assign a proficiency index to an individual to adjust a therapy or treatment display, according to one or more embodiments as shown and described herein.

In another embodiment, referring to FIG. 3, a method 300 may follow logic to, in block 302, receive from an individual at least one nutritional element content estimate of a food image 108. This receipt may be as part of a test for the individual to assign a proficiency index 111 as described herein. In block 304, the method may further follow logic to determine one or more deviation factors from the at least one nutritional element content estimate and a corresponding predetermined nutritional element content of the food image 108. In block 306, the method may further follow logic to assign the at least one proficiency index 111 to the individual based upon the one or more deviation factors, and, in block 308, adjust the treatment or therapy display 116 based on at least one nutritional element content estimate and at least one proficiency index 111.

In addition to the devices, systems also are provided that are configured for assigning to an individual a proficiency index classification. Additionally or alternatively, the systems can be configured for estimating nutritional element content of foods.

In some instances, the systems can include one or more devices such as a plurality of mobile devices and/or one or more computers that are configured for crowdsourcing nutritional element content estimates. Moreover, the systems can include remote devices, servers and cloud-based elements that communicate via wires or wirelessly (e.g., infrared, cellular, Bluetooth®), where such remote devices can be, for example, a local PC/server, or a remote PC/server or a cloud-based system.

Figure 4:
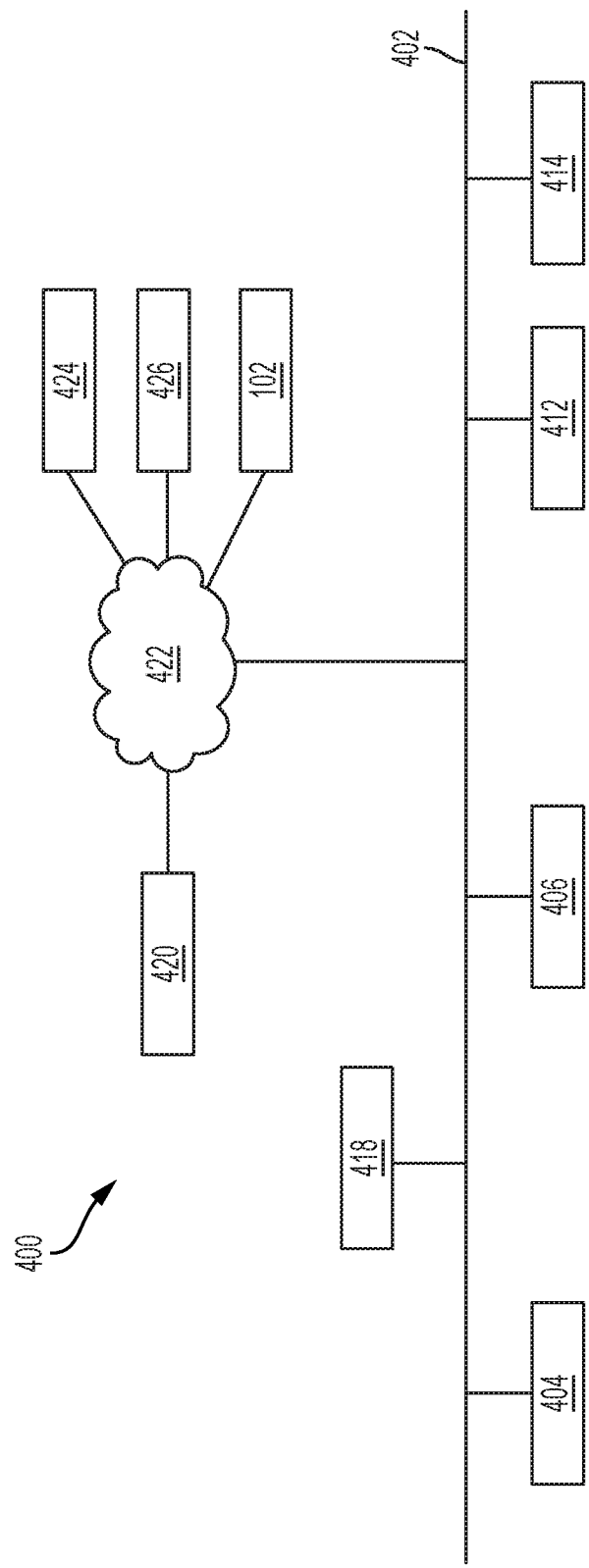
FIG. 4 schematically illustrates a system for implementing computer and software based methods to utilize the systems and methods of FIGS. 1-3, according to one or more embodiments shown and described herein.

Referring to FIG. 4, a system 400 for implementing a computer and software-based method with one or more devices as described herein, as shown in FIGS. 1-3, is illustrated and may be implemented along with using a graphical user interface (GUI) 424 that is accessible at a user workstation, e.g., a computing device and/or at the peripheral and central devices 102, 426, that may be medical devices each having their own GUIs, for example, and connected through a network 422 to utilize crowdsourcing methods as described herein. The system 400 includes a communication path 402, one or more processors 404, one or more memory components as memory 406, a proficiency index component 412, a storage or database 414, a network interface hardware 418, a server 420, a network 422, devices 102, 426, and the at least one GUI 424. The various components of the system 400 and the interaction thereof will be described in detail below.

While only one application server 420 and at least one GUI 424 of a workstation is illustrated, the system 400 can include multiple workstations and application servers containing one or more applications that can be located at geographically diverse locations. In some embodiments, the system 400 is implemented using a wide area network (WAN) or network 422, such as an intranet or the Internet, or other wired or wireless communication network that may include a cloud computing-based network configuration (for example, "the cloud"). The workstation computer including the GUI 424 may include digital systems and other devices permitting connection to and navigation of the network. Other system 400 variations allowing for communication between various geographically diverse components are possible. The lines depicted in FIG. 4 indicate communication rather than physical connections between the various components.

As noted above, the system 400 includes the communication path 1102. The communication path 402 may be formed from any medium that is capable of transmitting a signal such as, for example, conductive wires, conductive traces, optical waveguides, or the like, or from a combination of mediums capable of transmitting signals. The communication path 402 communicatively couples the various components of the system 400. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system 400 includes the one or more processors 404. The one or more processors 404 can be any device capable of executing machine readable instructions. Accordingly, the one or more processors 404 may be a controller, an integrated circuit, a microchip, a computer, or any other computing device. The one or more processors 404 is communicatively coupled to the other components of the system 400 by the communication path 402. Accordingly, the communication path 402 may communicatively couple any number of processors with one another, and allow the modules coupled to the communication path 402 to operate in a distributed computing environment. Specifically, each of the modules can operate as a node that may send and/or receive data. The one or more processors 404 may process the input signals received from the system modules and/or extract information from such signals.

As noted above, the system 400 includes the memory 406 which is coupled to the communication path 402 and communicatively coupled to the processor 404. The memory components 406 may be a non-transitory computer readable medium or non-transitory computer readable memory and may be configured as a nonvolatile computer readable medium. The memory 406 may comprise RAM, ROM, flash memories, hard drives, or any device capable of storing machine readable instructions such that the machine readable instructions can be accessed and executed by the one or more processors 404. The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the memory 406. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. In embodiments, the system 400 may include the one or more processors 404 communicatively coupled to the memory components 406 that stores instructions that, when executed by the one or more processors 404, cause the processor to perform one or more functions as described herein.

Still referring to FIG. 11, as noted above, the system 400 comprises the display such as a GUI 424 on a screen of a computing device for providing visual output such as, for example, information, graphical reports, messages, or a combination thereof. The computing device, such as devices 102, 426, may include one or more computing devices across platforms, or may be communicatively coupled to devices across platforms, such as mobile smart devices including smartphones, tablets, laptops, and/or the like or medical devices such as blood glucose meters, insulin pumps, continuous glucose monitors, and the like. The display on the screen of the computing device is coupled to the communication path 402 and communicatively coupled to the one or more processors 404. Accordingly, the communication path 402 communicatively couples the display to other modules of the system 400. The display can include any medium capable of transmitting an optical output such as, for example, a cathode ray tube, light emitting diodes, a liquid crystal display, a plasma display, or the like. Additionally, it is noted that the display or the computing device such as device 102, 426 can include at least one of the one or more processors 404 and the memory 406. While the system 400 is illustrated as a single, integrated system in FIG. 4, in other embodiments, the systems can be independent systems.

The system 400 comprises the proficiency index component 412 that in at least one embodiment is representative of a tool to assign and/or provide respective proficiency indexes as described herein. The proficiency index component 412 is coupled to the communication path 402 and communicatively coupled to the one or more processors 404. As will be described in further detail below, the one or more processors 404 may process the input signals received from the system modules and/or extract information from such signals.

The system 400 includes the network interface hardware 418 for communicatively coupling the system 400 with a computer network such as network 422. The network interface hardware 418 is coupled to the communication path 402 such that the communication path 402 communicatively couples the network interface hardware 418 to other modules of the system 400. The network interface hardware 418 can be any device capable of transmitting and/or receiving data via a wireless network. Accordingly, the network interface hardware 418 can include a communication transceiver for sending and/or receiving data according to any wireless communication standard. For example, the network interface hardware 418 can include a chipset (e.g., antenna, processors, machine readable instructions, etc.) to communicate over wired and/or wireless computer networks such as, for example, wireless fidelity (Wi-Fi), WiMax, BLUETOOTH®, IrDA, Wireless USB, Z-Wave, ZigBee, or the like.

Still referring to FIG. 4, data from various applications running on computing devices such as devices 102, 426 can be provided from the devices 102, 426 to the system 400 via the network interface hardware 418. The computing device can be any device having hardware (e.g., chipsets, processors, memory, etc.) for communicatively coupling with the network interface hardware 418 and a network 422. Specifically, the computing device can include an input device having an antenna for communicating over one or more of the wireless computer networks described above.

The network 422 can include any wired and/or wireless network such as, for example, wide area networks, metropolitan area networks, the Internet, an Intranet, the cloud, satellite networks, or the like. Accordingly, the network 422 can be utilized as a wireless access point by devices 102, 426 and/or workstation including GUI 424 to access one or more servers (e.g., a server 420). The server 420 and any additional servers generally include processors, memory, and chipset for delivering resources via the network 422. Resources can include providing, for example, processing, storage, software, and information from the server 420 to the system 400 via the network 422. Additionally, it is noted that the server 420 and any additional servers can share resources with one another over the network 422 such as, for example, via the wired portion of the network, the wireless portion of the network, or combinations thereof.

EXPERIMENTAL

The concept will be more fully understood upon consideration of the following non-limiting examples, which are offered for purposes of illustration, not limitation.

Example 1: Carbohydrate Counting Training and Testing

This example shows how an initial proficiency index can be determined and assigned to a group of individuals.

Methods and Results: A number of individuals are selected and shown at least three meals having predetermined carbohydrate contents. Each individual is asked to record a carbohydrate estimate for each meal.

The carbohydrate estimates for the individuals can be arranged as shown below in Table 1, where the first column includes a list of meals, where the second column includes the carbohydrate content for each meal, where subsequent columns include each individual's carbohydrate estimate.

TABLE 1

Data Layout for Estimates of Carbohydrate Content in Meals

| Meal | Carb Content | Individual 1 Estimate | Individual 2 Estimate | Individual 3 Estimate | ... | Individual N Estimate |
|---|---|---|---|---|---|---|
| 1 | 80 | 75 | 82 | 93 | ... | 74 |
| 2 | 120 | 100 | 95 | 110 | ... | 135 |
| 3 | 90 | 96 | 100 | 80 | ... | 85 |
| . | . | . | . | . | ... | . |
| . | . | . | . | . |  | . |
| . | . | . | . | . |  | . |
| M | $C_M$ | $C_{M1}$ | $C_{M2}$ | $C_{M3}$ | ... | $C_{MN}$ |

Table 2 shows the deviations of the received/recorded estimates of each individual from the corresponding actual/known carbohydrate content.

TABLE 2

Layout for Deviation Factor Determination

| Meal | Carb Content | Ind 1 Difference | Ind 2 Difference | Ind 3 Difference | ... | Ind N Difference |
|---|---|---|---|---|---|---|
| 1 | 80 | −5 | 2 | 13 | ... | −6 |
| 2 | 120 | −20 | −25 | −10 | ... | 15 |
| 3 | 90 | 6 | 10 | −10 | ... | −5 |
| . | . | . | . | . | ... | . |
| . | . | . | . | . |  | . |
| . | . | . | . | . |  | . |
| M | $C_M$ | $C_{M1} - C_M$ | $C_{M2} - C_M$ | $C_{M3} - C_M$ | ... | $C_{MN} - C_M$ |

For example, Individual 1 underestimated the carbohydrate content of meal 1 by 5 grams, Individual 2 overestimated the same meal by 2 grams, Individual 3 overestimated the same meal by 13 grams, and Individual N underestimated the same meal by 6 grams.

A proficiency index in the form of an EQ then can be calculated as noted elsewhere above for each individual as follows:

$$EQ_j = 1 / \sqrt{\frac{1}{M} \sum_{i=1}^{M} \left( \frac{100(c_{ij} - c_i)}{c_i} \right)^2}, \quad j = 1, 2, \ldots, N. \quad \text{(Equation 1)}$$

The properties of the proficiency index can be evaluated with a combination of statistical theory and simulations. For example, those individuals, J, with an expertness quotient, $EQ_j$, above predetermined threshold, $q_0$, are selected and used to evaluate unseen foods for carbohydrate content. The weighted average of those contents can be fed to a requester wishing to know the carbohydrate content of a food according to:

$$\overline{C} = \frac{EQ_1 c_1 + EQ_2 c_2 + \cdots + EQ_j c_j}{\Sigma EQ_j}. \quad \text{(Equation 2)}$$

All of the patents, patent applications, patent application publications and other publications recited herein are hereby incorporated by reference as if set forth in their entirety.

The present concept has been described in connection with what are presently considered to be the most practical and preferred embodiments. However, the concept has been presented by way of illustration and is not intended to be limited to the disclosed embodiments. Accordingly, one of skill in the art will realize that the concept is intended to encompass all modifications and alternative arrangements within the spirit and scope of the concept as set forth in the appended claims.

Numbered Embodiments

In addition or as an alternative to the above, the following embodiments are encompassed by the present disclosure and described as:

1. A method of assigning to an individual a proficiency index for estimating nutritional element content of foods, the method comprising the steps of:

(a). displaying to the individual a first plurality of food images to train the individual on estimating nutritional element content in foods, wherein nutritional element content of one or more nutritional elements in each food image is predetermined and displayed;

(b). displaying to the individual a second plurality of food images to test the individual on estimating nutritional element content in foods, wherein nutritional element content of one or more nutritional elements in each food image is predetermined and not displayed;

(c). receiving from the individual, nutritional element content estimates of nutritional elements in the second plurality of food images; and (d). determining one or more deviation factors from a difference between at least one nutritional element content estimate and a corresponding predetermined nutritional element content of the one or more nutritional elements in each food image and then assigning the proficiency index of the individual based upon the one or more deviation factors.

2. A method of assigning to an individual a proficiency index for estimating nutritional element content of foods, the method comprising the steps of:

(a). displaying to the individual a first plurality of food images to train the individual on estimating nutritional element content in foods, wherein nutritional element content of one or more nutritional elements in each food image is predetermined and not displayed;

(b). receiving or recording from the individual nutritional element content estimates of the first plurality of food images;

(c). providing to the individual the predetermined nutritional element content of the one or more nutritional elements in the first plurality of food images to permit learning or correcting;

(d). displaying to the individual a second plurality of food images to test the individual on estimating nutritional element content in foods, wherein nutritional element content of one or more nutritional elements in each food image is predetermined but not displayed;

(e). receiving from the individual, nutritional element content estimates of nutritional elements in the second plurality of food images; and (f). determining one or more deviation factors from a difference between at least one nutritional element content estimate and a corresponding predetermined nutritional element content of the one or more nutritional elements in each food image and then assigning the proficiency index of the individual based upon the one or more deviation factors.

3. A method of assigning to an individual a proficiency index for estimating nutritional element content of foods, the method comprising the steps of:

(a). displaying to the individual a plurality of food images to test the individual on estimating nutritional element content in foods, wherein nutritional element content of one or more nutritional elements in each food image is predetermined and not displayed;

(b). receiving from the individual, nutritional element content estimates of nutritional elements in the plurality of food images; and (c). determining one or more deviation factors from a difference between at least one nutritional element content estimate and a corresponding predetermined nutritional element content of the one or more nutritional elements in each food image and assigning the proficiency index of the individual based upon the one or more deviation factors.

4. The method of any one of Embodiments 1 to 3, wherein the proficiency index is a qualitative proficiency index.

5. The method of Embodiment 4, wherein the qualitative proficiency index is a level of expertise selected from the group consisting an expert estimator, an experienced estimator, and a beginner estimator.

6. The method of Embodiment 5, wherein the deviation factor for the expert estimator is 0-10, the deviation factor for the experienced estimator is 11-50, and the deviation factor for the beginner estimator is 51 and above.

7. The method of any one of Embodiments 1 to 3, wherein the proficiency index is a quantitative proficiency index.

8. The method of Embodiment 7, wherein the proficiency index is an expertness quotient calculated according to the following:

$$EQ_j = 1/\sqrt{\frac{1}{M}\sum_{i=1}^{M}\left(\frac{100(c_{ij} - c_i)}{c_i}\right)^2}, \ j = 1, 2, \ldots, N, \quad \text{(Equation 1)}$$

wherein M is a food image, N is an individual, $C_{ij}$ is the nutritional element content estimate and $C_i$ is the predetermined nutritional element content.

9. The method of any one of Embodiments 1 to 3, wherein the first plurality of food images and/or the second plurality of food images are manually displayed to the individual.

10. The method of any one of Embodiments 1 to 3, wherein the first plurality of food images and/or the second plurality of food images are electronically displayed to the individual.

11. The method of any one of Embodiments 1 to 2, wherein the nutritional elements are selected from the group consisting of (1) calories, carbohydrates, fats and proteins, (2) calories, carbohydrates and fats, (3) calories, carbohydrates and proteins (4) calories, fats and proteins, (5) carbohydrates, fats and proteins, (6) calories and carbohydrates, (7) calories and fats, (8) calories and proteins, (9) carbohydrates and fats, (10) carbohydrates and proteins, (11) fats and proteins, (12) calories, (13) carbohydrates, (14) fats, and (15) proteins.

12. The method of any one of Embodiments 1 to 3 further comprising the step of:

re-testing and re-assigning the proficiency index of the individual after a predetermined period of time by repeating steps (b)-(d) of Embodiment 1 or steps (d)-(f) of Embodiment 2.

13. The method of Embodiment 1 or 2, wherein the first plurality of food images and/or second plurality of food images comprises from about 5 food images to about 50 food images.

14. The method of Embodiment 13, wherein the first plurality of food images and/or second plurality of food images comprises about 25 food images.

15. The method of Embodiment 1 or 2, wherein each image in the first plurality of food images and/or second plurality of food images is displayed for about 5 seconds to about 60 seconds.

16. The method of Embodiment 15, wherein each image in the first plurality of food images and/or second plurality of food images is displayed for about 30 seconds.

17. A method of providing a nutritional element content estimate in a food image, the method comprising the steps of:

(a). displaying the food image to a plurality of individuals, wherein each of the plurality of individuals has a proficiency index that correlates to an ability to accurately and/or reliably provide the nutritional element content estimate in the food image, and wherein the proficiency index is assigned according to the method of any one of Embodiments 1 to 3;

(b). receiving from each of the plurality of individuals the nutritional element content estimate in the food image; and (c). calculating and displaying a weighted average of the nutritional element content estimates.

18. The method of Embodiment 17 further comprising the step of:

after receiving nutritional element estimates from each of the plurality of individuals, selecting only those nutritional element content estimates from individuals in the plurality of individuals having an assigned proficiency index above a predetermined threshold.

19. The method of Embodiment 17 or 18 further comprising the step of:

adjusting a treatment or a therapy for a disease or a disorder based upon the weighted average.

20. The method of Embodiment 19, wherein the treatment or therapy is insulin and the adjusting comprises increasing or decreasing an amount of insulin in an insulin dose.

21. The method of Embodiment 20 further comprising the step of:

administering to an individual the increased or decreased insulin dose.

22. The method of Embodiment 17 or 18 further comprising the step of:

initiating a treatment or a therapy for a disease or a disorder based upon the weighted average.

23. The method of Embodiment 22, wherein the treatment or therapy is insulin and the initiating comprises providing an amount of insulin in an insulin dose.

24. The method of any one of Embodiments 17 to 23, wherein the weighted average of the nutritional element content estimates is from a minimum of N individuals.

25. The method of Embodiment 24, wherein the minimum of N individuals is from about 5 individuals to about 50 individuals.

26. The method of Embodiment 25, wherein the minimum of N individuals is about 30 individuals.

27. The method of Embodiment 24, where the minimum of N individuals is from about 50 individuals to about 100 individuals.

28. The method of Embodiment 24, wherein the minimum of N individuals is greater than 100 individuals.

29. The method of any one of Embodiments 14 to 28 further comprising the step of:

displaying the weighted average of the nutritional element content estimates together with a confidence indicator to convey an expected reliability of the weighted average.

30. The method of any one of Embodiments 14 to 29 further comprising the step of:

re-testing and re-assigning the proficiency index of one or more individuals from the plurality of individuals after a predetermined period of time by repeating steps (b)-(d) of Embodiment 1 or steps (d)-(f) of Embodiment 2.

31. The method of any one of Embodiments 14 to 29 further comprising the step of:

randomly re-testing and re-assigning the proficiency index of one or more individuals from the plurality of individuals by repeating steps (b)-(d) of Embodiment 1 or steps (d)-(f) of Embodiment 2.

32. The method of any one of Embodiments 14 to 29, wherein the proficiency index is a qualitative proficiency index.

33. The method of Embodiment 32, wherein the qualitative proficiency index is a level of expertise selected from the group consisting an expert estimator, an experienced estimator, and a beginner estimator.

34. The method of Embodiment 33, wherein the deviation factor for the expert estimator is 0-10, the deviation factor for the experienced estimator is 11-50, and the deviation factor for the beginner estimator is 51 and above.

35. The method of any one of Embodiments 14 to 29, wherein the proficiency index is a quantitative proficiency index.

36. The method of Embodiment 35 wherein the proficiency index is an expertness quotient calculated according to the following:

$$EQ_j = 1 / \sqrt{\frac{1}{M}\sum_{i=1}^{M}\left(\frac{100(c_{ij}-c_i)}{c_i}\right)^2}, \quad j = 1, 2, \ldots, N, \quad \text{(Equation 1)}$$

wherein M is a food image, N is an individual, $C_{ij}$ is the nutritional element content estimate and $C_i$ is the predetermined nutritional element content.

37. A method of providing a weighted average of nutritional element content estimates in a food image, the method comprising the steps of:

(a). receiving a food image from a requestor on a primary device;

(b). electronically displaying the food image to a plurality of individuals on a plurality of secondary devices, wherein each of the plurality of individuals has a proficiency index assigned according to any one of the methods of Embodiments 1 to 3;

(c). receiving via wired or wireless means from the plurality of individuals their nutritional element content estimate in the food image;

(d). automatically calculating a weighted average of the received nutritional element content estimates; and (e) electronically displaying the weighted average of the nutritional element content estimates to the requestor on the primary device.

38. The method of Embodiment 37 further comprising the step of:

(f). after receiving nutritional element estimates from each of the plurality of individuals, selecting only those nutritional element content estimates from individuals in the plurality of individuals having an assigned proficiency index above a predetermined threshold.

39. The method of Embodiment 37 or 38 further comprising the step of:

(g). adjusting a treatment or a therapy for a disease or a disorder based upon the weighted average.

40. The method of Embodiment 39, wherein the treatment or therapy is insulin and the adjusting comprises increasing or decreasing an amount of insulin in an insulin dose.

41. The method of Embodiment 40 further comprising the step of:

(h). administering the increased or decreased insulin dose.

42. The method of Embodiment 37 or 38 further comprising the step of:

(g). initiating a treatment or a therapy for a disease or a disorder based upon the weighted average.

43. The method of Embodiment 42, wherein the treatment or therapy is insulin and the initiating comprises administering an amount of insulin in an insulin dose.

44. The method of any one of Embodiments 37 to 43, wherein the weighted average of the nutritional element content estimates is from a minimum of N individuals.

45. The method of Embodiment 44, wherein the minimum of N individuals is from about 5 individuals to about 50 individuals.

46. The method of Embodiment 45, wherein the minimum of N individuals is about 30 individuals.

47. The method of Embodiment 44, where the minimum of N individuals is from about 50 individuals to about 100 individuals.

48. The method of Embodiment 44, wherein the minimum of N individuals is greater than 100 individuals.

49. A computer-implemented method comprising the steps of:

(a). displaying to an individual a first plurality of food images to train the individual on estimating nutritional element content in foods, wherein nutritional element content of one or more nutritional elements in each food image is predetermined and displayed;

(b). displaying to the individual a second plurality of food images to test the individual on estimating nutritional element content in foods, wherein nutritional element content of one or more nutritional elements in each food image is predetermined and not displayed;

(c). receiving from the individual nutritional element content estimates of nutritional elements in the second plurality of food images; and (d). determining one or more deviation factors from a difference between at least one nutritional element content estimate and a corresponding predetermined nutritional element content of the one or more nutritional elements in each food image and assigning the proficiency index of the individual based upon the one or more deviation factors.

50. A computer-implemented method comprising the steps of:

(a). displaying to an individual a first plurality of food images to train the individual on estimating nutritional element content in foods, wherein nutritional element content of one or more nutritional elements in each food image is predetermined and not displayed;

(b). receiving or recording from the individual nutritional element content estimates of the first plurality of food images;

(c). providing to the individual the predetermined nutritional element content of the one or more nutritional elements in the first plurality of food images to permit learning or correcting;

(d). displaying to the individual a second plurality of food images to test the individual on estimating nutritional element content in foods, wherein nutritional element content of one or more nutritional elements in each food image is predetermined but not displayed;

(e). receiving from the individual nutritional element content estimates of nutritional elements in the second plurality of food images; and (f). determining one or more deviation factors from a difference between at least one nutritional element content estimate and a corresponding predetermined nutritional element content of the one or more nutritional elements in each food image and then assigning the proficiency index of the individual based upon the one or more deviation factors.

51. A computer-implemented method comprising the steps of:

(a). displaying to the individual a plurality of food images to test the individual on estimating nutritional element content in foods, wherein nutritional element content of one or more nutritional elements in each food image is predetermined and not displayed;

(b). receiving from the individual nutritional element content estimates of nutritional elements in the second plurality of food images; and (c). determining one or more deviation factors from a difference between at least one nutritional element content estimate and a corresponding predetermined nutritional element content of the one or more nutritional elements in each food image and then assigning the proficiency index of the individual based upon the one or more deviation factors.

52. A computer-implemented method comprising the steps of:

(a). displaying a food image to a plurality of individuals, wherein each of the plurality of individuals has a proficiency index that correlates to an ability to provide a nutritional element content estimate in the food image, and wherein the proficiency index is assigned according to the method of any one of Embodiments 1 to 3;

(b). receiving from each of the plurality of individuals the nutritional element content estimate in the food image; and (c). calculating and displaying a weighted average of the nutritional element content estimates.

53. A non-transitory computer-readable medium comprising program instructions for causing an electronic device to execute a method comprising the steps of:

(a). displaying to an individual a first plurality of food images to train the individual on estimating nutritional element content in foods, wherein nutritional element content of one or more nutritional elements in each food image is predetermined and displayed;

(b). displaying to the individual a second plurality of food images to test the individual on estimating nutritional element content in foods, wherein nutritional element content of one or more nutritional elements in each food image is predetermined and not displayed;

(c). receiving from the individual nutritional element content estimates of nutritional elements in the second plurality of food images; and (d). determining one or more deviation factors from a difference between at least one nutritional element content estimate and a corresponding predetermined nutritional element content of the one or more nutritional elements in each food image and then assigning the proficiency index of the individual based upon the one or more deviation factors.

54. A non-transitory computer-readable medium comprising program instructions for causing an electronic device to execute a method comprising the steps of:

(a). displaying to an individual a first plurality of food images to train the individual on estimating nutritional element content in foods, wherein nutritional element content of one or more nutritional elements in each food image is predetermined and not displayed;

(b). receiving or recording from the individual nutritional element content estimates of the first plurality of food images;

(c). providing to the individual the predetermined nutritional element content of the one or more nutritional elements in the first plurality of food images to permit learning or correcting;

(d). displaying to the individual a second plurality of food images to test the individual on estimating nutritional element content in foods, wherein nutritional element content of one or more nutritional elements in each food image is predetermined but not displayed;

(e). receiving from the individual nutritional element content estimates of nutritional elements in the second plurality of food images; and (f). determining one or more deviation factors from a difference between at least one nutritional element content estimate and a corresponding predetermined nutritional element content of the one or more nutritional elements in each food image and assigning the proficiency index of the individual based upon the one or more deviation factors.

55. A non-transitory computer-readable medium comprising program instructions for causing an electronic device to execute a method comprising the steps of:

(a). displaying a food image to a plurality of individuals, wherein each of the plurality of individuals has a proficiency index that correlates to an ability to provide a nutritional element content estimate in the food image, and wherein the proficiency index is assigned according to the method of any one of Embodiments 1 to 3;

(b). receiving from each of the plurality of individuals the nutritional element content estimate in the food image; and (c). calculating and displaying a weighted average of the nutritional element content estimates.

56. A non-transitory computer-readable medium comprising instructions which, when the computer-readable storage medium is executed by a computer, causes the computer to carry out the steps of the method of any one of Embodiments 1 to 48.

57. A computer program product comprising instructions which, when the computer program is executed by a computer, causes the computer to carry out the steps of the method of any one of Embodiments 1 to 48.

58. An electronic device application comprising instructions which, when the application is executed by an electronic device, causes the electronic device to carry out the steps of the method of any one of Embodiments 1 to 48.

59. An electronic device for improved nutritional element content estimates, the electronic device comprising:

a processor, a memory, and a transceiver, wherein the processor is configured to:

(a). display to an individual a first plurality of food images to train the individual on estimating nutritional element content in foods, wherein nutritional element content of one or more nutritional elements in each food image is predetermined and displayed;

(b). display to the individual a second plurality of food images to test the individual on estimating nutritional element content in foods, wherein nutritional element content of one or more nutritional elements in each food image is predetermined and not displayed;

(c). receive from the individual nutritional element content estimates of nutritional elements in the second plurality of food images; and (d). determine one or more deviation factors from a difference between at least one nutritional element content estimate and to a corresponding predetermined nutritional element content of the one or more nutritional elements in each food image and assigning the proficiency index of the individual based upon the one or more deviation factors.

60. A data processing device or system comprising means for carrying out the method of any one of Embodiments 1 to 48.

61. A method of assigning to an individual a proficiency classification for estimating nutritional element content of foods as substantially described and shown herein.

62. A method of providing a nutritional element content estimate in a food image via crowdsourcing as substantially described and shown herein.

63. A computer-implemented method of assigning to an individual a proficiency classification for estimating nutritional element content of foods as substantially described and shown herein.

64. A computer-implemented method of providing a nutritional element content estimate in a food image via crowdsourcing as substantially described and shown herein.

65. A computer-implemented method of assigning to an individual a proficiency classification for estimating nutritional element content of foods as substantially described and shown herein.

66. A computer-implemented method of providing a nutritional element content estimate in a food image via crowdsourcing as substantially described and shown herein.

67. A device for assigning to an individual a proficiency classification for estimating nutritional element content of foods as substantially described and shown herein.

68. A device for providing a nutritional element content estimate in a food image via crowdsourcing as substantially described and shown herein.

69. A system for assigning to an individual a proficiency classification for estimating nutritional element content of foods as substantially described and shown herein.

70. A system for providing a nutritional element content estimate in a food image via crowdsourcing as substantially described and shown herein.

The invention claimed is:

1. An improved graphical user interface (GUI) of a nutritional estimation tool on an electronic device with a memory and one or more processors to execute one or more programs stored in the memory for determining a therapy or treatment based on a nutritional element content estimate and improving diabetes management, the improved GUI operatively coupled to the one or more processors, the improved GUI comprising:

a therapy or treatment display based on at least one nutritional element content estimate and at least one proficiency index to improve accuracy and reliability when estimating nutritional element content in foods and therapy or treatment based therefrom;

wherein the one or more processors are operatively coupled to an insulin pump;

wherein the one or more processors are adapted to execute computer implemented instructions to:

receive a plurality of nutritional element content estimates of a food image from a plurality of individuals correlated to a respective plurality of proficiency indexes, wherein each nutritional element content estimate from an individual is correlated to a respective proficiency index for the individual corresponding to a pre-determined ability of the individual to accurately and reliably provide the nutritional element content estimate in the food image, wherein each proficiency index in the plurality of proficiency indexes is a quantitative proficiency index comprising an expertness quotient (EQ) calculated according to the following:

$$EQ_j = 1/\sqrt{\frac{1}{M}\sum_{i=1}^{M}\left(\frac{100(c_{ij}-c_i)}{c_i}\right)^2}, j = 1, 2, \ldots, N$$

wherein M is the food image, N is an integer number of the plurality of individuals, $C_{ij}$ is the nutritional element content estimate, and $C_i$ is a predetermined nutritional element content;

calculate a weighted average of the plurality of nutritional element content estimates based on the respective plurality of proficiency indexes;

display the weighted average on the improved GUI;

adjust the therapy or treatment display based on the weighted average;

adjust the therapy or treatment for based upon the therapy or treatment display through one of an increase or a decrease of an amount of insulin in an adjusted insulin dose, wherein the therapy or treatment is for a disease or a disorder for the individual; and administer the adjusted insulin dose to the individual through the insulin pump.

2. The improved GUI of claim 1, wherein the one or more processors are further adapted to execute computer implemented instructions to: select a selected portion of the plurality of nutritional element content estimates received from the plurality of individuals that correlates to a respective plurality of proficiency indexes that are each above a predetermined threshold; and calculate the weighted average of the plurality of nutritional element content estimates based on the selected portion of the plurality of nutritional element content estimates.

3. The improved GUI of claim 1, wherein the one or more processors are further adapted to execute computer implemented instructions to: display a confidence indicator of the weighted average of the plurality of nutritional element content estimates together with the weighted average to convey an expected reliability of the weighted average.

* * * * *